United States Patent
Marsh et al.

(10) Patent No.: US 9,109,591 B2
(45) Date of Patent: Aug. 18, 2015

(54) METHODS AND SYSTEMS FOR DOSING CONTROL IN AN AUTOMATED FLUID DELIVERY SYSTEM

(71) Applicant: MEDRAD, INC., Indianola, PA (US)

(72) Inventors: Charles Marsh, Cranberry Township, PA (US); Larry McCutchan, Allison Park, PA (US)

(73) Assignee: Bayer Medical Care Inc., Indianola, PA (US)

( * ) Notice: Subject to any disclaimer, the term of this patent is extended or adjusted under 35 U.S.C. 154(b) by 279 days.

(21) Appl. No.: 13/784,615

(22) Filed: Mar. 4, 2013

(65) Prior Publication Data

US 2014/0248159 A1 Sep. 4, 2014

(51) Int. Cl.

| | |
|---|---|
| *F04B 7/02* | (2006.01) |
| *F04B 43/02* | (2006.01) |
| *F04B 43/12* | (2006.01) |
| *F04B 49/06* | (2006.01) |
| *F04B 49/10* | (2006.01) |

(52) U.S. Cl.
CPC ................ *F04B 43/02* (2013.01); *F04B 43/12* (2013.01); *F04B 49/065* (2013.01); *F04B 49/106* (2013.01)

(58) Field of Classification Search
USPC ................ 222/63, 55, 1; 417/53, 302; 600/4; 604/507; 137/1
See application file for complete search history.

(56) References Cited

U.S. PATENT DOCUMENTS

| | | | |
|---|---|---|---|
| 5,217,355 A | | 6/1993 | Hyman et al. |
| 6,616,633 B1 * | | 9/2003 | Butterfield et al. ........... 604/151 |
| 8,632,487 B2 * | | 1/2014 | Gunther et al. ............. 604/6.15 |
| 2002/0019714 A1 * | | 2/2002 | Carliale et al. .................. 702/73 |
| 2003/0199803 A1 * | | 10/2003 | Robinson et al. ............ 604/6.04 |
| 2005/0145010 A1 * | | 7/2005 | Vanderveen et al. .......... 73/1.57 |
| 2009/0099498 A1 * | | 4/2009 | Demers et al. .............. 604/6.09 |
| 2009/0131862 A1 * | | 5/2009 | Buck et al. ...................... 604/67 |
| 2010/0280430 A1 * | | 11/2010 | Caleffi et al. ................ 604/5.01 |
| 2011/0178359 A1 * | | 7/2011 | Hirschman et al. .............. 600/4 |
| 2011/0209764 A1 * | | 9/2011 | Uber et al. ......................... 137/1 |
| 2011/0264011 A1 * | | 10/2011 | Wu et al. ........................... 601/2 |
| 2012/0073673 A1 * | | 3/2012 | Kameyama .................... 137/14 |
| 2014/0046295 A1 * | | 2/2014 | Uber et al. .................... 604/507 |
| 2014/0228617 A1 * | | 8/2014 | Agamaite ......................... 600/4 |

FOREIGN PATENT DOCUMENTS

| | | |
|---|---|---|
| EP | 1616587 | 1/2006 |
| WO | 9923386 | 5/1999 |

OTHER PUBLICATIONS

The International Search Report and the Written Opinion from corresponding PCT Application No. PCT/US2014/019430 mailed Jun. 24, 2014.

* cited by examiner

*Primary Examiner* — Donnell Long
(74) *Attorney, Agent, or Firm* — Joseph L. Kent; David Schramm; James R. Stevenson

(57) ABSTRACT

Methods and systems for dispensing a fluid using an automated fluid delivery system are disclosed. A pump may be configured to force an aliquot of fluid into a fluid delivery channel. A processor may receive values of a property for the aliquot and the source of the aliquot. The processor may use the values to determine the volume of the aliquot. The determined volume is compared by the processor against an expected volume to establish the amount of fluid being pumped by the pump per unit, such as time or revolutions. The processor controls operation of the pump to dispense a predetermined dose based on the amount of fluid being pumped by the pump per unit.

19 Claims, 5 Drawing Sheets

METHODS AND SYSTEMS FOR DOSING CONTROL IN AN AUTOMATED FLUID DELIVERY SYSTEM

BACKGROUND

Automated fluid delivery systems, such as infusion systems, operate to administer medication to a patient in carefully measured doses. Such infusion systems may deliver fluids in a manner that is often more cost effective and reliable than if performed manually by medical staff. Accurate dosing is important, especially for particular fluids, such as radiopharmaceuticals where high precision is required to ensure that the patient is not exposed to too much radioactive material. Typical automated infusion systems pump the fluid using an infusion pump through a delivery tube and into a patient's venous system through a needle or catheter. A common infusion pump is the peristaltic pump that operates by deforming the delivery tube to force the fluid from a fluid source toward the patient.

The automated infusion process is often controlled using various parameters, such as infusion rate and duration, dose volume, patient weight, and medication units and concentration. However, these parameters are affected by the specific components and operating characteristics of the infusion system equipment. Conventional automated dosing techniques do not adequately adjust for these variances, which may lead to inaccurate delivery of medical fluids to patients.

SUMMARY

The invention described in this document is not limited to the particular systems, methodologies or protocols described, as these may vary. The terminology used herein is for the purpose of describing particular embodiments only, and is not intended to limit the scope of the present disclosure.

It must be noted that as used herein and in the appended claims, the singular forms "a," "an," and "the" include plural reference unless the context clearly dictates otherwise. Unless defined otherwise, all technical and scientific terms used herein have the same meanings as commonly understood by one of ordinary skill in the art. As used herein, the term "comprising" means "including, but not limited to."

In an embodiment, a system for dispensing a fluid may comprise a pump configured to force an aliquot of fluid from a fluid source into a fluid delivery channel and at least one sensor configured to measure a sample value of a property of the aliquot. A computing device in communication with the pump and the at least one sensor may comprise a processor and a non-transitory, computer-readable storage medium in operable communication with the processor. The computer-readable storage medium may contain one or more programming instructions that, when executed, cause the processor to: receive the sample value, receive a source value of the property for the fluid source, determine a sample volume of the aliquot based on a comparison of the sample value and the source value, and control operation of the pump to dispense a predetermined dose of the fluid based on a comparison of the sample volume with an expected volume.

In an embodiment, a method of dispensing a fluid may comprise providing a pump configured to force an aliquot of fluid from a fluid source into a fluid delivery channel. A processor may receive a source value of a property for the fluid source and a sample value of the property for the aliquot measured by at least one sensor. The processor may determine a volume of the aliquot based on a comparison of the sample value of the property and the source value of the property. The operation of the pump may be controlled by the processor to dispense a predetermined dose of the fluid based on a comparison of the sample volume with an expected volume.

DETAILED DESCRIPTION

The terminology used in the description is for the purpose of describing the particular versions or embodiments only, and is not intended to limit the scope.

The present disclosure is directed toward dosage control in an automated fluid delivery system, such as an automated infusion system. In one embodiment, a fluid delivery pump is used to pump a fluid being delivered to a patient through the automated fluid delivery system. An illustrative and non-restrictive example of a fluid delivery pump is a peristaltic pump. According to some embodiments, the automated fluid delivery system may compare a property of the fluid in a fluid source with the same property of the fluid in a fluid delivery channel of the automated fluid delivery system. This comparison may be used to determine the sample volume of the fluid in the fluid delivery channel. This volume may be compared with an expected or standard volume to correlate operation of the pump with volume of the fluid pumped into the fluid delivery channel. The automated fluid delivery system may operate to control the pump based on this comparison. In an embodiment, the automated fluid delivery system may be configured to deliver a radiopharmaceutical. In this embodiment, the property may comprise radioactivity of a volume of the radiopharmaceutical. A non-limiting example of an automated fluid delivery system is the Intego™ positron emission tomography (PET) infusion system provided by Bayer Medical Care Inc. of Indianola, Pa.

Figure 1:
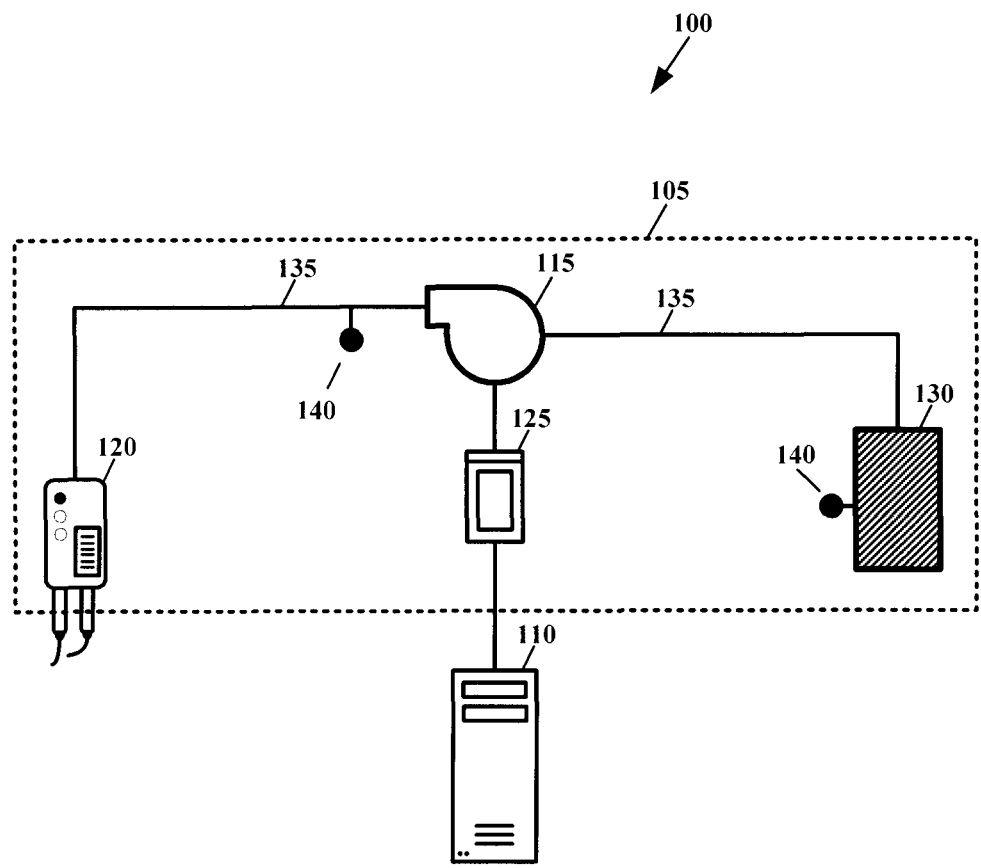
FIG. 1 depicts an illustrative automated fluid delivery system according to an embodiment.

FIG. 1 depicts an illustrative automated fluid delivery system according to an embodiment. As shown in FIG. 1, an automated fluid delivery system 100 may include a fluid delivery apparatus 105 configured to deliver a medical fluid to a patient. In an embodiment, the fluid delivery apparatus 105 may comprise an infusion apparatus. The fluid delivery apparatus 105 may have a medical fluid source 130 arranged therein and configured to hold a volume of the medical fluid. For example, some diagnostic imaging procedures, such as PET and single-photon emission computed tomography (SPECT), require that a patient receive radioactive contrast agents, also called radiopharmaceuticals, to obtain images. In a radiopharmaceutical infusion system, the medical fluid source 130 may be in the form of a shielded vial or "pig," such as a tungsten shielded vial. In another example, the medical fluid source 130 may comprise an infusion bag, such as an intravenous (IV) bag. Embodiments provide that the medical fluid may comprise any fluid capable of being delivered to a patient through an automated fluid delivery system, including, without limitation, saline, chemotherapy drugs, radiopharmaceuticals, and contrast agents.

The medical fluid source 130 may be in fluid communication with a pump 115 through a fluid delivery channel 135. Although the medical fluid source 130 is depicted in FIG. 1 as being located within the fluid delivery apparatus 105, embodiments are not so limited. The medical fluid source 130 may be located outside of the fluid delivery apparatus 105 in fluid communication with the fluid delivery apparatus through the fluid delivery channel 135. Accordingly, the fluid delivery channel 135 may be located at least partially outside of the fluid delivery apparatus 105. Some embodiments provide that the fluid delivery channel 135 may include more than one section and the sections may have different characteristics. For example, the fluid delivery channel 135 may be made of one type of material and have a particular diameter, thickness, or other property at a certain section and may be made of another material and/or have a different diameter, thickness, or other property at a different section.

Operation of the pump 115 draws the fluid out of the medical fluid source 130 and pumps it toward a dispensing element 120. Embodiments may be configured to operate with any type of pump known to those having ordinary skill in the art or that may be developed in the future that may operate as described herein. Illustrative pumps include, without limitation, turbine pumps, peristaltic pumps, diaphragm pumps, screw pumps, syringe pumps, and centrifugal pumps. The dispensing element 120 may be configured to deliver the medical fluid to a patient through the fluid delivery channel 135, such as a needle or catheter.

A controller 125 may be in communication with the pump 115. The controller 125 may generally comprise a processor, a non-transitory memory or other storage device for housing programming instructions, data or information regarding one or more applications, and other hardware, including, for example, the central processing unit (CPU) 605, read only memory (ROM) 610, random access memory 615, communication ports 640, controller 620, and/or memory device 625 depicted in FIG. 6 and described below in reference thereto. The controller 125 may be configured to receive information from the pump 115, such as the speed of the pump. Certain aspects of the pump 115 may be directed by the controller 125, such as the number of rotations, speed, linear travel distance, and/or active status (e.g., on/off, energized/de-energized, active/idle, etc.). In an embodiment, the controller 125 may execute pump control software configured to control operation of the pump 115. For example, the control software may be configured to operate the pump for a specified amount of time, number of rotations, or linear travel distance to displace a particular volume of the medical fluid.

The fluid delivery apparatus 105 may be operatively coupled with a computing device 110. Embodiments provide that the computing device 110 may comprise the illustrative internal hardware depicted in FIG. 6 and described below in reference thereto. In an embodiment, the computing device 110 comprises a pump controller. In another embodiment, the computing device 110 comprises a stand-alone computing device in communication with the fluid delivery apparatus 105. The computing device 110 may be configured to store or access data associated with operation of the fluid delivery apparatus 105, such as patient information, medical fluid information, and operational information of apparatus components. The data may be stored in one or more databases on the computing device 110 and/or in a medical information system accessible by the computing device.

Figure 4:
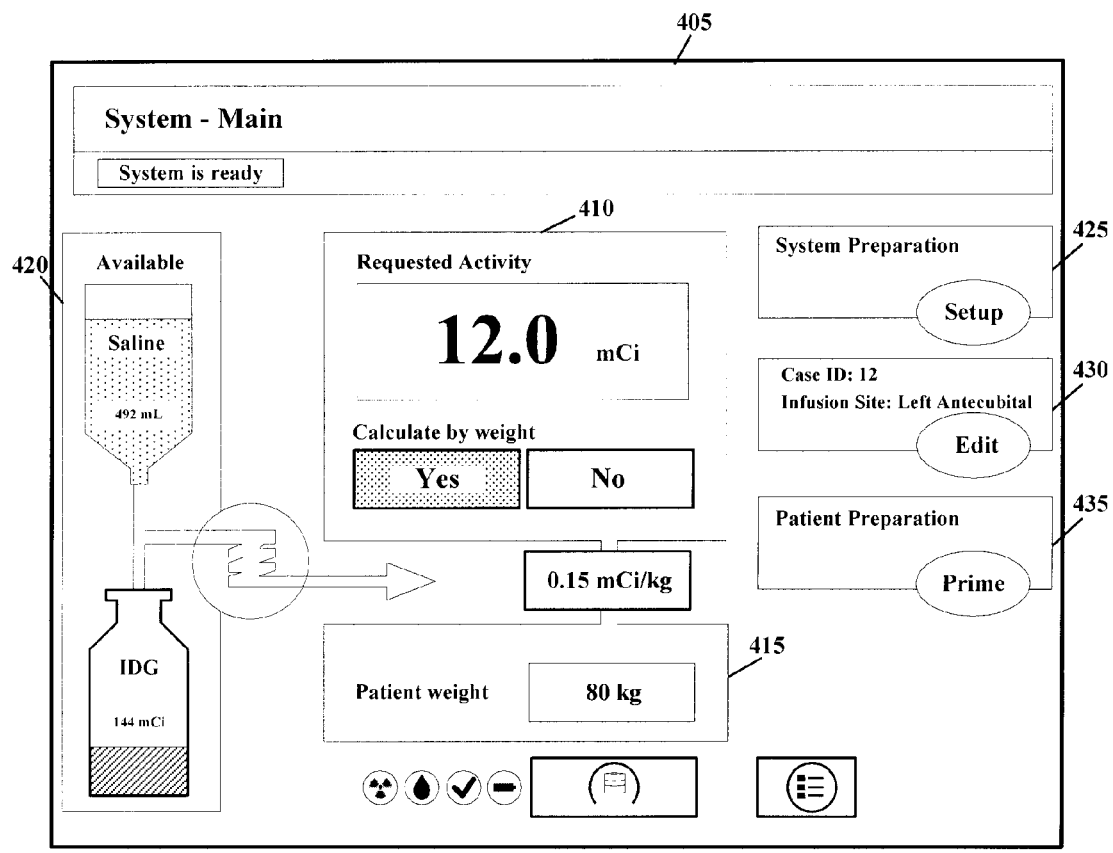
FIG. 4 depicts an illustrative automated fluid delivery system control screen according to some embodiments.

In an embodiment, the computing device 110 may execute one or more software programs (e.g., control software) for operating the fluid delivery apparatus 105. For example, the one or more software programs may present a user interface on a display device (not shown) connected to the computing device 110 for medical staff operation of the fluid delivery apparatus 105. For instance, an operator may start and/or stop infusion and view information associated with the infusion process from the user interface. An illustrative user interface is depicted in FIG. 4 and described in more detail below. According to some embodiments, the computing device 110 may be in communication with the controller 125. The computing device 110 may receive information from the controller 125, such as pump control information, and may provide for operator control of the pump 115 directly or through the controller 125. In an embodiment, the control software may operate to control the automated fluid delivery system and/or components thereof. For instance, the control software may be configured to direct the controller 125 and/or the pump 115 to operate for a specified amount of time, number of rotations, linear travel distance, or any other type of pump operation capable of controlling the displacement of a particular volume of the medical fluid.

One or more sensors 140 may be positioned in and/or around the fluid delivery apparatus 105 to obtain information associated with the medical fluid. The one or more sensors 140 may be positioned at various places, such as in or around the medical fluid source 130, the fluid delivery channel 135, or any other location suitable to obtain information about the medical fluid as it travels through the fluid delivery apparatus 105. The one or more sensors 140 may include any type of sensor capable of measuring a property of interest, including, without limitation, concentration, radioactivity, salinity, conductance, optical properties, analyte concentration, and combinations thereof. Illustrative sensors include, but are not limited to, temperature sensors, pressure sensors, radioactivity sensors, optical sensors, analyte sensors, concentration sensors, flow sensors, and combinations thereof. The computing device 110 and/or the controller 125 may be in communication with the one or more sensors 140 such that they may receive information detected by the one or more sensors, for example, for use by software applications executing on the computing device and/or the controller.

According to some embodiments, information obtained from the one or more sensors 140 (e.g., "sensor information") may be used alone or in combination with other available information to determine properties about the medical fluid being dispensed by the fluid delivery apparatus 105. This information may be used to determine, for instance, whether the correct dose of the medical fluid is being dispensed to a patient. In one embodiment, the sensor information may be used in combination with fluid data, such as historical data or data calculated by one or more software programs being executed by the computing device 110. In an embodiment, the sensor information may comprise information about the medical fluid in the fluid delivery channel 135 and the fluid data may comprise information about the medical fluid in the medical fluid source 130 or historical data relating thereto.

Figure 2:
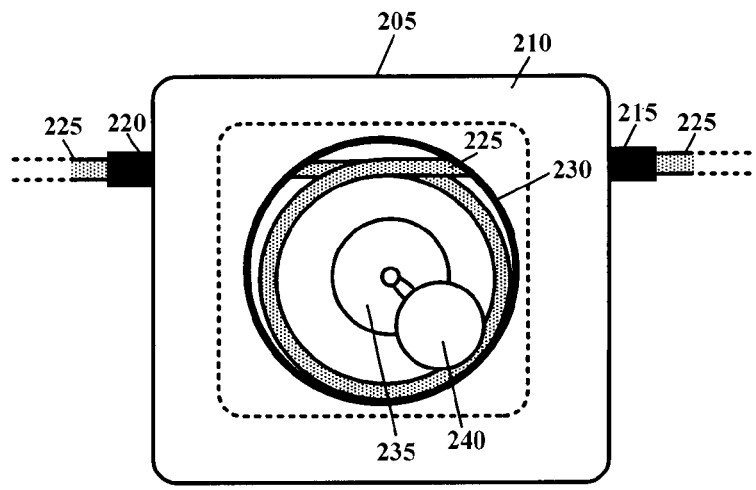
FIG. 2 depicts an illustrative peristaltic pump that may be used in automated fluid delivery systems configured according to some embodiments.

Embodiments described herein may include automated fluid delivery systems, such as an automated fluid delivery system, comprising various types of pumps. FIG. 2 depicts an illustrative peristaltic pump that may be used in automated fluid delivery systems according to some embodiments. As shown in FIG. 2, a peristaltic pump 205 may include a pump casing 210 housing a rotor 235. A fluid delivery channel 225 may enter the pump casing 210 through an inlet 215, coil around the inside of the pump casing, and exit through an outlet 220. In an embodiment, the fluid delivery channel 225 may comprise a flexible and deformable tube, such as a polyvinyl chloride (PVC) tube. The fluid delivery channel 225 may be in fluid communication with a source of a medical fluid (not shown) on the inlet 215 side and a fluid dispensing unit (not shown) on the outlet 220 side.

The rotor 235 may be connected to a roller 240 that rotates with rotor. The roller 240 may be in contact with the fluid delivery channel 225 within the housing 210, compressing the fluid delivery tube at the point of contact. This compression in combination with the rotation of the rotor 235 forces the medical fluid through the fluid delivery channel 225 from the inlet 215 toward the outlet 220. Embodiments are not limited to the particular rotor 235 and roller 240 configuration depicted in FIG. 2, as other peristaltic pump rotors may operate according to embodiments described herein. For example, the rotor itself, or one or more portions thereof, may be configured to be in contact with a fluid delivery channel in a manner similar to the roller 240 depicted in FIG. 2. In another example, the rotor 235 and/or the roller 240 may include fins, rollers or other components configured to provide smooth compression and fluid delivery through the fluid delivery channel 225.

The amount of fluid progressing through the fluid delivery channel 225 is dependent on, among other things, the rotational speed of the rotor 235, degree of rotation or number of rotations of rotor 235, and the cross-sectional area of the fluid delivery channel. In some instances, pumping efficiency may be related to occlusion of the fluid delivery channel 225, which may be a function of the wall thickness of the fluid delivery channel and the minimum gap between the rotor and the interior 230 of the pump casing 210. In a conventional medical infusion system, the speed of the fluid delivery pump, or infusion pump, may be fixed as it is generally assumed that the dimensional properties of the fluid delivery channels do not vary appreciably across manufacturers or even within the same manufacturer. Illustrative dimensional properties that may vary between different fluid delivery channels include outer diameter, wall thickness, and inner diameter. In addition, process variation in the production of a fluid delivery channel may also lead to variability in properties thereof. As such, dimensional properties may vary along the length of the fluid delivery channel itself. Changes in these properties will have an effect on the amount of medical fluid delivered through the fluid delivery channel for a given speed and/or rotational distance of the pump rotor. Such process variation may lead to significant errors in fluid volume delivery, especially for fine control of small volumes of medical fluid.

Figure 3:
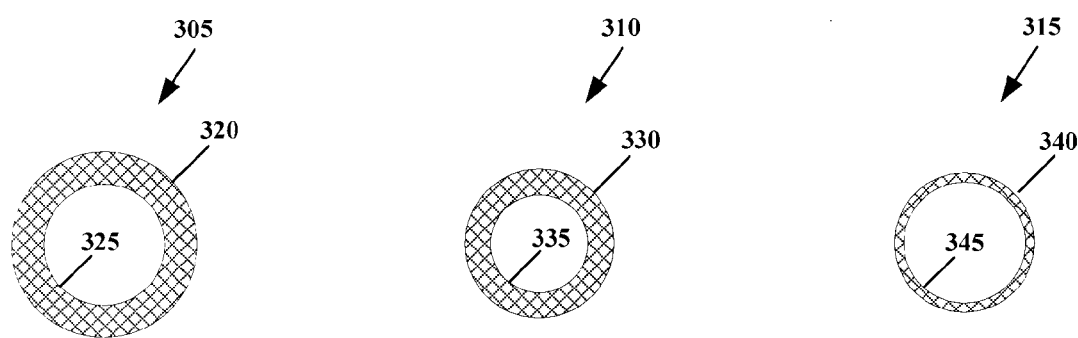
FIG. 3 depicts illustrative fluid delivery channels having different dimensional properties.

FIG. 3 depicts illustrative fluid delivery channels having different dimensional properties. As shown in FIG. 3, fluid delivery channels 305, 310, 315 may have different dimensional properties, such as wall thickness, inner diameter, and outer diameter. For instance, a fluid delivery pump of an automated fluid delivery system may have been designed to operate with the "standard" outer diameter 330 and inner diameter 335 of fluid delivery channel 310. In addition, the control software of the automated fluid delivery system may have been configured to control the fluid delivery pump with a fluid delivery channel having such standard dimensional properties. The thickness of a fluid delivery channel may be calculated by (outer diameter−inner diameter)/2 and the cross-sectional area may be calculated by $\pi((\text{inner diameter})/2)^2$. The amount of fluid pumped through a fluid delivery channel will be affected by the thickness and cross-sectional area thereof. For instance, for an automated fluid delivery system using a peristaltic pump, such as the peristaltic pump depicted in FIG. 2, the thickness of the fluid delivery channel may affect the amount of compression by the rotor or roller. The cross-sectional area may affect the volume of fluid travelling through the fluid delivery channel for a given pump speed.

Fluid delivery channel 305 may have the same inner diameter 325 as standard fluid delivery channel 310, but may have a greater outer diameter 320. As such, fluid delivery channel 305 may have the same cross-sectional area, but will have a different thickness. Fluid delivery channel 315 may have a greater inner diameter 345 and a smaller outer diameter 340 than standard fluid delivery channel 310. Accordingly, fluid delivery channel 315 may have a greater cross-sectional area and a smaller thickness than standard fluid delivery channel 305. The variability of fluid delivery channel dimensional properties may lead to unknown changes in fluid flow through the fluid delivery channel. Due to this variability, it is necessary to adjust the control of the pump to provide a consistent volume regardless of the dimensional properties of the fluid delivery channel.

FIG. 4 depicts an illustrative automated fluid delivery system control screen according to some embodiments. As shown in FIG. 4, an automated fluid delivery system control screen 405 may be configured to display fluid delivery information such as the amount of available medical fluid 420, requested medical fluid properties 410, and patient information 415. The embodiment depicted in FIG. 4 is for an automated fluid delivery system, such as an automated infusion system, configured to deliver a radiopharmaceutical to a patient. As such, the medical fluid information 420 may comprise information about the volume of the radiopharmaceutical and any fluids being combined therewith, the requested fluid properties 410 may comprise the requested radioactivity, and the patient information 415 may comprise the patient weight. The control screen 405 may provide one or more functions to an automated fluid delivery system operator, such as system preparation 425, procedure information 430 and patient preparation 435. In addition, various other fluid delivery process control functions and information may be presented to an operator through the control screen 405, such as functions to start or stop the process, access data, and/or verify the configuration of the process.

According to some embodiments, the control screen 405 may be presented on a display device operatively coupled with a computing device in communication with the automated fluid delivery system, such as the computing device 110 and the fluid delivery apparatus 105 depicted in FIG. 1. The control screen 405 may be in communication with or may be a component of control software configured to operate the automated fluid delivery system and/or components thereof (e.g., the pump and/or pump controller).

It is important to ensure that a patient receives a proper dose of the medical fluid during the fluid delivery process. As such, the control of the fluid delivery pump should be established before the patient begins to receive the medical fluid through the automated fluid delivery system. According to some embodiments, adjustment of the operation of the fluid delivery pump may be managed through the control software configured to operate the automated fluid delivery system and/or components thereof. The operation of the fluid delivery pump may need to be adjusted, for instance, due to variations in the dimensional properties of the fluid delivery channel. Embodiments provide that adjustments to the operation of the fluid delivery pump may be implemented when the fluid delivery channel is being primed with the medical fluid, such as through the patient preparation 435 function available from the control screen 405. Priming allows the fluid delivery channel to be pre-filled with fluid before injection, preventing unwanted air from being introduced into the patient's vasculature.

In an embodiment, the fluid delivery pump may be a peristaltic pump used to deliver a radiopharmaceutical to a patient through the automated fluid delivery system. Illustrative and non-restrictive examples of radiopharmaceuticals include $^{64}$Cu diacetyl-bis(N4-methylthiosemicarbazone) (e.g., ATSM or Copper 64), $^{18}$F-fluorodeoxyglucose (FDG), $^{18}$F-fluoride, 3'-deoxy-3'-[$^{18}$F]fluorothymidine (FLT), $^{18}$F-fluoromisonidazole (FMISO), gallium, technetium-99m, indium-113m, strontium-87m, and thallium.

The control software may be configured to turn the rotor a specified number of whole or partial rotations to displace a specified volume (e.g., an aliquot) of the radiopharmaceutical. The number of whole or partial rotations determined by the control software may be based on one or more pump coefficients, such as a volume-per-revolution coefficient. In another embodiment, the control software may be configured to operate the pump for a specified time based on a volume-per-time coefficient as the pump coefficient. The radioactivity of any particular volume of the radiopharmaceutical may be measured along the path of the fluid delivery channel using one or more sensors (such as sensors 140 depicted in FIG. 1). Non-limiting examples of sensors include silicon diodes, silicon PIN diode radiation sensors, avalanche diodes, scintillators, photomultipliers, solid state crystals, semiconductors, Geiger tubes, ionization-chamber radiation detectors, silicon photodiodes, microdischarge-based radiation detectors, sodium iodide crystal radiation detectors, bismuth tri-iodide crystal radiation detectors, or cadmium tellurium and cadmium zinc tellurium semiconductor crystal radiation detectors, and combinations thereof.

The peristaltic pump may rotate the specified number of whole or partial rotations, for example, when priming the fluid delivery channel, to displace a volume of the radiopharmaceutical into the fluid delivery channel. The aliquot of radiopharmaceutical displaced in the fluid delivery channel may be measured for a sample value of the property, such as sample total radioactivity. The source value of the property, such as source radioactivity of the radiopharmaceutical stored in the medical fluid source may be received by the control software. For example, the medical fluid source radioactivity may be measured by a sensor, ma: be entered into the control software by an operator, and/or may be determined by a formula (e.g. based on the radioactivity when delivered to the medical facility and the time between delivery and infusion). If the activity of the radiopharmaceutical in the medical fluid source from which the aliquot was extracted is known, then the sample total radioactivity in the aliquot may be used to determine the aliquot volume. The calculated volume of the aliquot may be compared with ar expected volume by the control software. The control software may then rescale or adjust the pump coefficient value for the volume-per-revolution coefficient according to the measured radioactivity of the aliquot.

According to embodiments, the process for determining the proper pump coefficient, such as the volume-per-revolution coefficient or the volume-per-time coefficient may be performed for each fluid delivery channel set, may be performed multiple times to determine a statistical average, and/or may be performed before each new patient.

The control software may have use default pump coefficient ($C_d$), for example, based on operating the fluid delivery pump under standard conditions. In one embodiment, $C_d$ may be used to calculate a corrected pump coefficient ($C_c$) using, for example, the measured sample value or a property, such as, radioactivity of the radiopharmaceutical (M), standard pump movement (K) and assay concentration (A) according to the following: $C_c=M/(K\times A)$. Embodiments provide that $C_c$ and $C_d$ may represent volume-per-revolution coefficients, for instance, having units of milliliters (mL)/revolution, M may have units of mCi or MBq, and A may have units of mCi/mL or MBq/mL. In another embodiment, $C_c$ may be determined by applying an alpha ($\alpha$) filter mechanism to $C_d$ instead of through direct measurement.

The variable K may have units that depend on the type of fluid delivery pump. For example, for a peristaltic pump, the units of K may have units of pump revolutions. In another example, K may have units of encoder counts or linear travel distance for a syringe pump. In essence, $C_c$ may be configured as a measure of a volume/native pump movement metric used to command the pump. In a non-limiting example, a target dose T may comprise the target dose amount wherein dosing is volume based, and the pump may be commanded to pump a certain volume in mL using the following equation: pump revolutions=$C_c$(mL/rev)*[T (mCi)/A (mCi/mL)]. This process may provide an intermediate estimate of volume for fluid accounting, which may rely on an accurate estimate of A for proper dose measurement. According to some embodiments, $C_c$ may be measured directly when setting up a fluid delivery system using a small number of known motor movements as opposed to assuming a default value $C_d$ and applying corrections after a dose intended for patient fluid delivery has already been extracted.

In an embodiment, an alpha filter may be used with multiple measurements to arrive at a final coefficient. For instance, instead of assigning $C_c$=M/K×A directly, $C_c[n]$ may be set as $C_c[n]=C_c[n-1]*(1-\text{alpha})+\text{alpha}*M/K\times A$, where alpha is a value between 0 and 1. This process may converge slower, but may prevent a single measurement from causing the measurement system to destabilize. In general, the process may operate to average multiple readings into the final corrected coefficient instead of making a direct assignment based on a single reading.

As described herein, embodiments may provide for activity-based dosing as opposed to conventional volume-based dosing. An automated fluid delivery system may be configured to tune dosage volumes based on concentration measurements. In an embodiment, dosing measurements may comprise a plot of activity ingress to achieve optimal amount of dose in the fluid delivery channel and as a visual indication of these measurements, for instance, for fault diagnosis. For example, $T=(C_d)(K)(A)$ and $M=(C_c)(K)(A)$ and, therefore, $T=MC_d/C_c$. The following may be formulated based on the foregoing calculations: $C_c=((M)(C_d))/T=((M)(C_d))/((C_d)(K)(A))$.

For activity based dosing, $C_c$ may be measured during the initial concentration check as $C_c=M/K$. In an embodiment, M/K may have units of mCi/rev. In another embodiment, the activity measurements may be MBq, mCi, or other concentration units and the units of native motor motion may depend on the type of pump and control mechanism, as described above. For example, M/K may have units of mCi/millimeter for a syringe pump. In activity based dosing, the motor may be commanded to move $T/C_c$ revolutions to extract the proper dose amount, allowing for accurate dosing without an accurate or less accurate estimate of source concentration A. In a non-limiting example, the coefficient may be tuned using the process $C_c(\text{new})=C_c(\text{current})*M/T$, where M is the measured activity and T is the target activity. This correction process may be applied when dosing regardless of the dosing method (e.g., regardless of the units of $C_c$).

Figure 5:
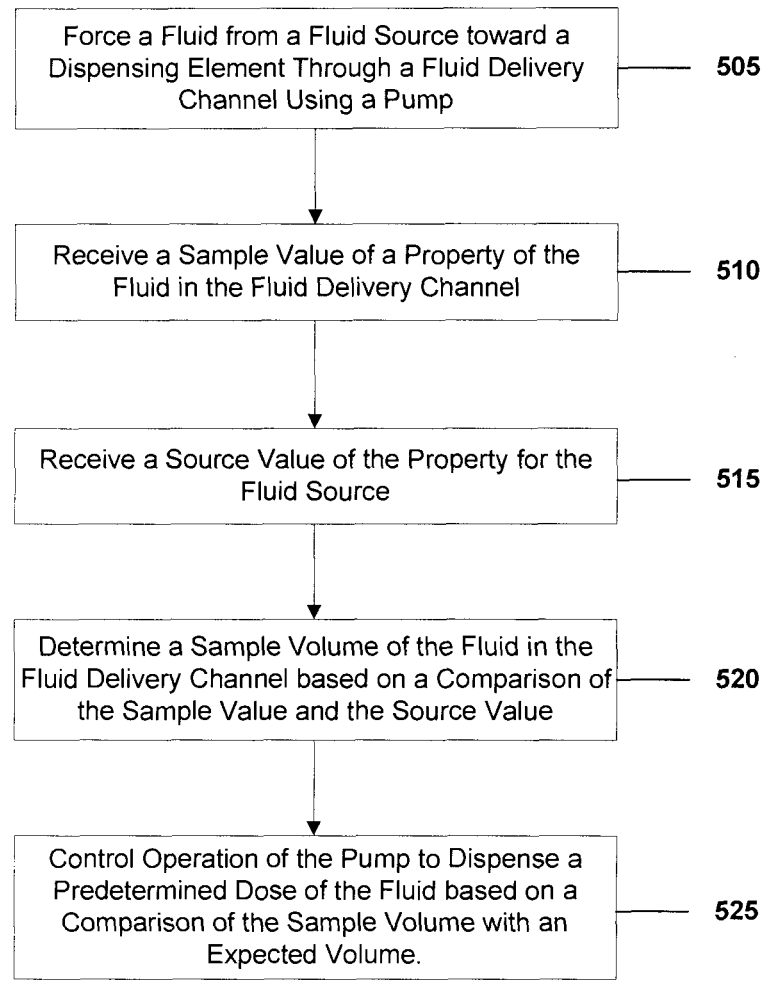
FIG. 5 depicts a flow diagram of a method of dispensing a fluid according to an embodiment.

FIG. 5 depicts a flow diagram of a method of dispensing a fluid according to an embodiment. As shown in FIG. 5, a fluid may be forced 505 from a fluid source toward a dispensing element through a fluid delivery channel using a pump. For example, a peristaltic pump may rotate a specified number of rotations to move an aliquot of a medical fluid into a fluid delivery channel from a fluid source. In an embodiment, the specified number of rotations may be enough to move a sample volume of the fluid into the fluid delivery channel and not enough to dispense the fluid to a patient. The medical fluid may comprise a radiopharmaceutical, such as a contrast agent for a nuclear imaging procedure. A processor may receive 510 a sample value of a property of the fluid in the fluid delivery tube. For a radiopharmaceutical, the sample value may comprise the radioactivity of the aliquot in the fluid delivery channel as measured by one or more sensors accessible by the processor. A source value of the property for the fluid source may be received 515 by the processor. The source value may be obtained from the fluid source through various methods, including through measurement by a sensor, data entry by an operator, calculation based on properties of the fluid source, and combinations thereof.

The processor may determine 520 a sample volume of the fluid in the fluid delivery channel based on a comparison of the sample value and the source value. For instance, the radioactivity of the fluid source may be compared with the radioactivity of the fluid in the fluid delivery channel to determine the volume of the fluid in the fluid delivery channel. Operation of the pump may be controlled 525 to dispense a predetermined dose of the fluid based on comparing the sample volume with an expected volume. For example, the comparison of the sample volume and the expected volume may be used to adjust, calibrate, or otherwise correct the operation of the pump to dispense a predetermined dose of the fluid to a patient. For instance, automated fluid delivery system control software may be configured to rotate the pump rotor X times to dispense a predetermined amount (e.g., mL, mCi, etc.) of the fluid to achieve the predetermined dose. The amount of the fluid required for the dose may depend on various factors, such as whether the dose is determined by concentration, radioactivity, and the like. For example, for a radiopharmaceutical, the dose may be an amount of radioactivity, while for a medicine in solution, the dose may be a particular volume (e.g., mL) of the fluid. The comparison of the sample volume with the expected volume may reveal that rotating the pump rotor X times may dispense more/less than the predetermined dose. As such, the number of times to rotate the pump rotor may be adjusted by the control software to rotate the pump rotor the correct number of times (e.g., X×adjustment coefficient) to dispense the predetermined amount of the fluid.

Figure 6:
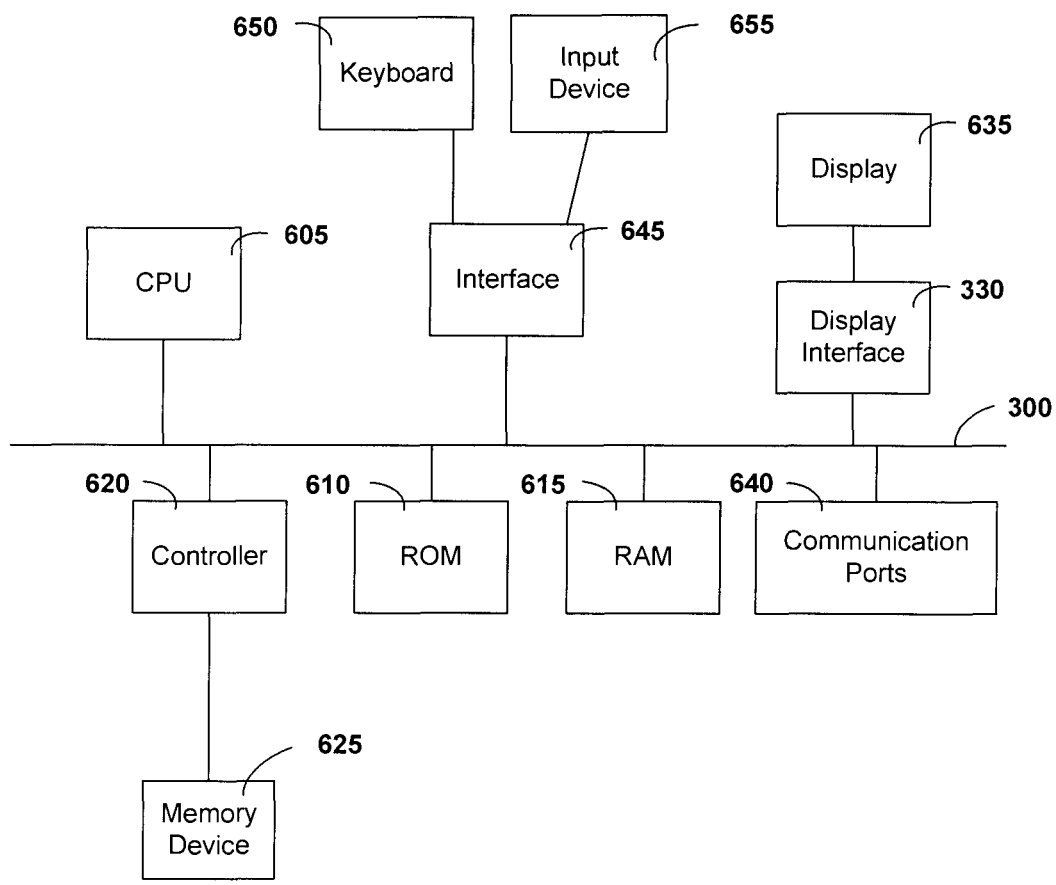
FIG. 6 depicts a block diagram of illustrative internal hardware that may be used to contain or implement program instructions according to an embodiment.

FIG. 6 depicts a block diagram of exemplary internal hardware that may be used to contain or implement program instructions, such as the process steps discussed above in reference to FIG. 5, according to an embodiment. A bus 600 serves as the main information highway interconnecting the other illustrated components of the hardware. CPU 605 is the central processing unit of the system, performing calculations and logic operations required to execute a program. CPU 605, alone or in conjunction with one or more of the other elements disclosed in FIGS. 1 and 6, is an exemplary processing device, computing device or processor as such terms are using in this disclosure. Read only memory (ROM) 610 and random access memory (RAM) 615 constitute exemplary memory devices.

A controller 620 interfaces with one or more optional memory devices 625 to the system bus 600. These memory devices 625 may include, for example, an external or internal DVD drive, a CD ROM drive, a hard drive, flash memory, a USB drive or the like. As indicated previously, these various drives and controllers are optional devices.

Program instructions, software or interactive modules for providing the digital marketplace and performing analysis on any received feedback may be stored in the ROM 610 and/or the RAM 615. Optionally, the program instructions may be stored on a tangible computer readable medium such as a compact disk, a digital disk, flash memory, a memory card, a USB drive, an optical disc storage medium, such as a Blu-ray™ disc, and/or other recording medium.

An optional display interface 630 may permit information from the bus 600 to be displayed on the display 635 in audio, visual, graphic or alphanumeric format. Communication with external devices may occur using various communication ports 640. An exemplary communication port 640 may be attached to a communications network, such as the Internet or an intranet. Other exemplary communication ports 640 may comprise a serial port, a RS-232 port, and a RS-485 port.

The hardware may also include an interface 645 which allows for receipt of data from input devices such as a keyboard 650 or other input device 655 such as a mouse, a joystick, a touch screen, a remote control, a pointing device, a video input device and/or an audio input device.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

What is claimed is:

1. A system for dispensing a radiopharmaceutical fluid, comprising:
    a pump configured to force an aliquot of a radiopharmaceutical fluid from a fluid source into a fluid delivery channel;
    at least one radioactivity sensor configured to measure a sample value of a radioactivity property of the aliquot;
    a processor in communication with the pump and the at least one radioactivity sensor; and
    a non-transitory, computer-readable storage medium in operable communication with the processor, wherein the computer-readable storage medium contains one or more programming instructions that, when executed, cause the processor to:
    receive the sample value,
    receive a source value of the radioactivity property for the fluid source,
    determine a sample volume of the aliquot based on a comparison of the sample value and the source value;
    determine a pump coefficient based on a comparison of the sample volume with an expected volume, wherein the pump coefficient is configured to indicate a volume of fluid forced into the fluid delivery channel per unit; and
    control operation of the pump to dispense a predetermined dose of the radiopharmaceutical fluid based on the comparison of the sample volume with the expected volume.

2. The system of claim 1, wherein the pump coefficient comprises a volume-per-time coefficient.

3. The system of claim 1, wherein the pump coefficient comprises a volume-per-revolution coefficient.

4. The system of claim 1, wherein the one or more programming instructions that, when executed, cause the processor to control operation of the pump further comprise one or more programming instructions that, when executed, cause the processor to control operation of the pump using the pump coefficient.

5. The system of claim 1, wherein the one or more programming instructions that, when executed, cause the processor to control operation of the pump further comprise one or more programming instructions that, when executed, cause the processor to adjust the pump coefficient to correspond with dispensing the predetermined dose.

6. The system of claim 1, wherein the expected volume comprises a volume of the radiopharmaceutical fluid forced by the pump under standard conditions.

7. The system of claim 1, wherein the pump is selected from the group consisting of a turbine pump, a peristaltic pump, a diaphragm pump, a screw pump, a syringe pump, and a centrifugal pump.

8. The system of claim 1, wherein the non-transitory, computer-readable storage medium comprises a remote operated touch screen.

9. The system of claim 1, wherein the pump comprises a peristaltic pump arranged to contact at least a portion of the fluid delivery channel such that operation of the pump compresses the at least a portion of the fluid delivery channel and forces the radiopharmaceutical fluid through the fluid delivery channel from the fluid source toward a dispensing element,
wherein the sample volume of the aliquot is affected by at least one dimensional property of the fluid delivery channel.

10. The system of claim 9, wherein the at least one dimensional property comprises an inner diameter.

11. The system of claim 9, wherein the at least one dimensional property comprises an outer diameter.

12. A method of dispensing a radiopharmaceutical fluid, comprising:
providing a pump configured to force an aliquot of a radiopharmaceutical fluid from a fluid source into a fluid delivery channel;
receiving, by a processor, a source value of a radioactivity property for the fluid source and a sample value of the radioactivity property for the aliquot measured by at least one radioactivity sensor;
determining, by the processor, a sample volume of the aliquot based on a comparison of the sample value of the radioactivity property and the source value of the radioactivity property;
determining, by the processor, a pump coefficient based on a comparison of the sample volume with an expected volume, wherein the pump coefficient is configured to indicate a volume of fluid forced into the fluid delivery channel per unit; and
controlling, by the processor, operation of the pump to dispense a predetermined dose of the radiopharmaceutical fluid based on the comparison of the sample volume with the expected volume.

13. The method of claim 12, wherein the pump coefficient comprises a volume-per-time coefficient.

14. The method of claim 12, wherein the pump coefficient comprises a volume-per-revolution coefficient.

15. The method of claim 12, wherein controlling operation of the pump further comprises controlling the pump using the pump coefficient.

16. The method of claim 12, wherein controlling operation of the pump further comprises adjusting the pump coefficient to correspond with dispensing the predetermined dose.

17. The method of claim 12, wherein the expected volume comprises a volume of the radiopharmaceutical fluid forced by the pump under standard conditions.

18. The method of claim 12, wherein the pump is selected from the group consisting of a turbine pump, a peristaltic pump, a diaphragm pump, a screw pump, a syringe pump, and a centrifugal pump.

19. The method of claim 12, further comprising:
inputting data to the processor by a remote operated touch screen, wherein the data is in regard to one or more of the receiving step, the determining the sample volume step, the determining the pump coefficient step, and the controlling step.

* * * * *

UNITED STATES PATENT AND TRADEMARK OFFICE
CERTIFICATE OF CORRECTION

PATENT NO. : 9,109,591 B2
APPLICATION NO. : 13/784615
DATED : August 18, 2015
INVENTOR(S) : Marsh et al.

It is certified that error appears in the above-identified patent and that said Letters Patent is hereby corrected as shown below:

IN THE SPECIFICATION:
In Column 5, Line 9, delete "housing 210," and insert -- housing --, therefor.
In Column 7, Line 44, delete "ma:" and insert -- may --, therefor.
In Column 8, Line 64, delete "Ce(new)" and insert -- Cc(new) --, therefor.

Signed and Sealed this
Twenty-eighth Day of June, 2016

Michelle K. Lee
*Director of the United States Patent and Trademark Office*